United States Patent
Silverman et al.

(10) Patent No.: US 9,878,996 B2
(45) Date of Patent: Jan. 30, 2018

(54) 2-IMIDAZOLYL-PYRIMIDINE SCAFFOLDS AS POTENT AND SELECTIVE INHIBITORS OF NEURONAL NITRIC OXIDE SYNTHASE

(71) Applicant: Northwestern University, Evanston, IL (US)

(72) Inventors: Richard B. Silverman, Winnetka, IL (US); Paramita Mukherjee, Evanston, IL (US); Hien M. Nguyen, Iowa City, IA (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/602,833

(22) Filed: May 23, 2017

(65) Prior Publication Data
US 2017/0260165 A1    Sep. 14, 2017

Related U.S. Application Data

(62) Division of application No. 14/798,307, filed on Jul. 13, 2015, now Pat. No. 9,701,661.

(60) Provisional application No. 62/023,746, filed on Jul. 11, 2014.

(51) Int. Cl.
*C07D 403/04* (2006.01)
*A61K 31/506* (2006.01)
*C07D 401/14* (2006.01)
*C07D 401/04* (2006.01)

(52) U.S. Cl.
CPC .......... *C07D 403/04* (2013.01); *A61K 31/506* (2013.01); *C07D 401/04* (2013.01); *C07D 401/14* (2013.01)

(58) Field of Classification Search
CPC ............................ C07D 403/04; A61K 31/506

USPC .......................................... 544/331; 514/275
See application file for complete search history.

(56) References Cited

U.S. PATENT DOCUMENTS

| 7,470,790 B2 | 12/2008 | Silverman et al. |
| 2006/0116515 A1 | 6/2006 | Gahman et al. |
| 2008/0108814 A1 | 5/2008 | Silverman et al. |

FOREIGN PATENT DOCUMENTS

| WO | 2010057101 A2 | 5/2010 |
| WO | 2012139043 A2 | 10/2012 |

OTHER PUBLICATIONS

Chemical Abstract Compound, STN express. RN 1241139-23-0 (Entered STN: Sep. 15, 2010).
Chemical Abstract Compound, STN express. RN 1311896-58-8 (Entered STN: Jul. 7, 2011) and RN 1258746-84-7 (Entered STN: Jan. 7, 2011).
Chemical Abstract Compound, STN express. RN 1444378-30-6 (Entered STN: Jul. 16, 2013).
Mukherjee, P., et al., "Novel 2, 4-disubstituted pyrimidines as potent, selective, and cell-permeable inhibitors of neronal nitric oxide synthase", Journal of Medicinal chemistry, Dec. 2014, vol. 58, No. 3, pp. 1067-1088.
International Search Report for PCT/US2015/040216 dated Jun. 22, 2016.
Written Opinion for PCT/US2015/040216 dated Jun. 22, 2016.
International Preliminary Report on Patentability for PCT/US2015/040216 dated Jan. 26, 2017.

*Primary Examiner* — Deepak Rao
(74) *Attorney, Agent, or Firm* — Andrus Intellectual Property Law, LLP

(57) ABSTRACT

Imidazolyl-pyrimidine and related compounds, as can utilize heme-iron coordination in the selective inhibition of neuronal nitric oxide synthase.

20 Claims, 6 Drawing Sheets

Figure 1:
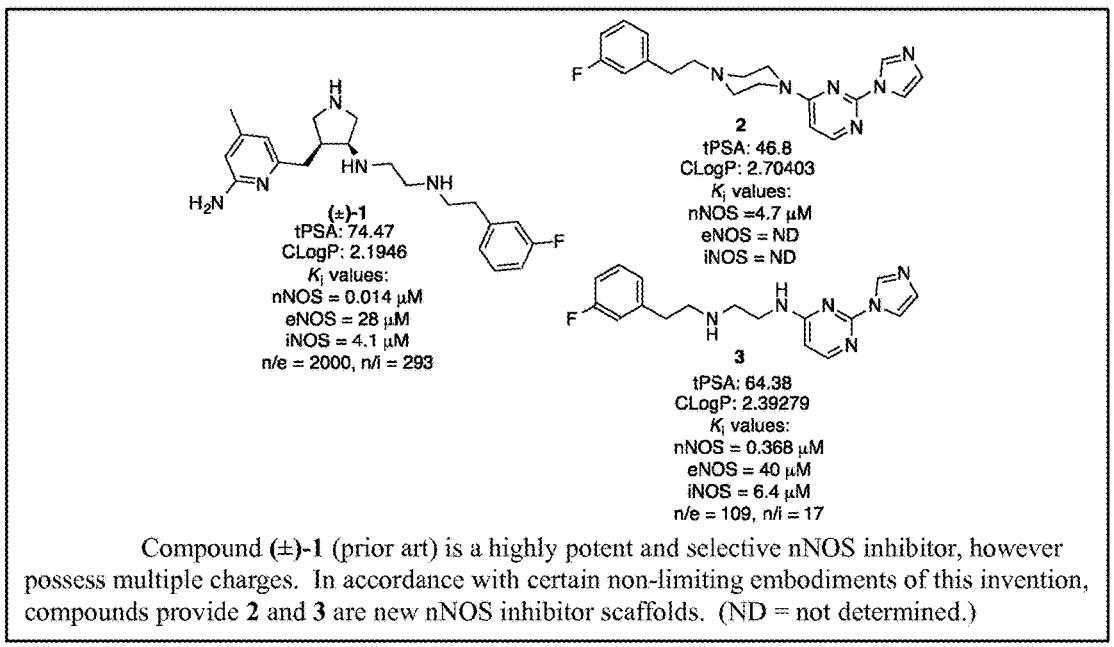

Compound (±)-1 (prior art) is a highly potent and selective nNOS inhibitor, however possess multiple charges. In accordance with certain non-limiting embodiments of this invention, compounds provide 2 and 3 are new nNOS inhibitor scaffolds. (ND = not determined.)

X-ray crystallographic binding mode of 7 in the oxygenase domain of nNOS (left) and eNOS (right). Polar interactions are shown by dashed lines.

Modifications on compound 7 can be employed to improve n/i selectivity, minimize CYP inhibition, and improve human nNOS potency, respectively, such compounds also in accordance with the present invention.

2-IMIDAZOLYL-PYRIMIDINE SCAFFOLDS AS POTENT AND SELECTIVE INHIBITORS OF NEURONAL NITRIC OXIDE SYNTHASE

This application is a divisional application of U.S. application Ser. No. 14/798,307, filed on Jul. 13, 2015, and published as U.S. Publication No. 2016/0009690, on Jan. 14, 2016, which application claims priority to and the benefit of application Ser. No. 62/023,746 filed Jul. 11, 2014—the entirety of which is incorporated herein by reference.

This invention was made with government support under R01 GM049725 awarded by the National Institutes of Health. The government has certain rights in the invention.

BACKGROUND OF THE INVENTION

Nitric oxide (NO) is a cell signaling molecule that acts as a neurotransmitter in the human brain. However, under neurodegenerative conditions, when the level of nitric oxide increases several folds of magnitude, various disease states can result. For instance, high levels of NO contribute to the damage of brain tissue, protein aggregation and degradation of the sort associated with various neurodegenerative disease states including but not limited to Alzheimer's disease, Parkinson's disease, Huntington's disease, amyotrophic lateral sclerosis (ALS), cerebral palsy and stroke/ischemic brain damage. By inhibiting the enzyme that produces NO in the brain, neuronal nitric oxide synthase (nNOS), neurodegeneration can be attenuated or prevented. However, most inhibitor compounds investigated to date are mimics of the natural substrate of nNOS, the amino acid L-arginine. Such compounds are basic and highly charged under physiological conditions, adversely affecting blood-brain barrier (BBB) permeation. In addition, designing useful nNOS inhibitors requires selectivity over two enzyme isoforms, inducible NOS (iNOS) and endothelial NOS (eNOS) to avoid unintended negative side effects. Accordingly, there remains an on-going concern in the art to develop new molecular scaffolds, with improved BBB permeability for selective nNOS inhibition.

SUMMARY OF THE INVENTION

In light of the foregoing, it is an object of the present invention to provide compounds and related methods for the selective inhibition of nNOS, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide a range of imidazolyl pyrimidine-based compounds for the study of nNOS inhibition.

It can also be an object of the present invention to provide such compounds for use in an nNOS binding mode utilizing heme-Fe coordination in the active site of the nNOS enzyme.

It can also be an object of the present invention alone or in conjunction with one or more of the preceding objectives, to provide such compounds exhibiting improved physical and chemical parameters of the sort for enhanced bioavailability and blood-brain barrier permeation, en route to the treatment of various neurodegenerative disease states.

Other objects, features, benefits and advantages of the present invention will be apparent from this summary and the following descriptions of certain embodiments, and will be readily apparent to those skilled in the art having knowledge of various nitric oxide synthase inhibitor compounds and synthetic techniques for their preparation. Such objects, features, benefits and advantages will be apparent from the above, as taken into conjunction with the accompanying examples, data, figures and all reasonable inferences to be drawn therefrom, alone or with consideration of the references incorporated herein.

In part, the present invention can be directed to compounds of formula

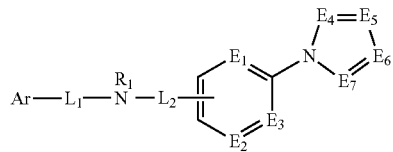

wherein Ar can be selected from optionally-substituted aryl and heteroaryl moieties, where such substituents can be selected from halo, alkyl, haloalkyl, cyano and amino substituents; $L_1$ can be selected from optionally-substituted divalent $C_1$-$C_4$ alkylene moieties, where such substituents can be selected from halo, alkyl and divalent methylene substituents; $R_1$ can be selected from H, alkyl and divalent alkylene substituents; $L_2$ can be selected from optionally-substituted divalent $C_1$-$C_3$ alkylene moieties, where such substituents can be selected from halo, aza (—NH—) and substituted aza (—$NR_2$) moieties, where $R_2$ can be selected from alkyl and divalent alkylene substituents; $E_1$-$E_3$ can be independently selected from CH and N; and $E_4$-$E_7$ can be independently selected from CH, $CR_3$ and N, providing at least one of $E_4$-$E_7$ is N, and where $R_3$ can be selected from methyl and halo substituents, and salts of such a compound.

Such aryl and heteroaryl moieties as can be selected from moieties of the sort described, inferred herein or as would otherwise be understood by those skilled in the art and made aware of this invention. Without limitation, Ar can be selected from fluoro-, chloro- and cyano-substituted phenyl moieties, pyridinyl, methyl- and methyl- and amino-substituted pyridinyl moieties. Regardless, in certain embodiments, $L_1$ can be selected from $(CH_2)_n$ moieties, where n can be an integer selected from 1-3, $CH(R_4)CH(R_5)CH(R_6)$ moieties where each of $R_4$-$R_6$ can be independently selected from H, fluoro, and alkyl substituents and moieties where $R_4$ and $R_5$ can together and $R_5$ and $R_6$ can together form methylene substituents and cyclopropyl moieties. In certain such embodiments, $L_2$ can be selected from $(CH_2)_m$, $CH(R_7)CH(R_8)$, $(CH_2)_m NH$ and $(CH_2)_m NR_2$ moieties, where m can be an integer selected from 1-3 and each of $R_7$-$R_8$ can be independently selected from H and fluoro substituents, and moieties where $R_1$ and $R_2$ can together form a divalent $C_1$-$C_2$ alkylene substituent and a diazacycloalkyl moiety. As a separate consideration, $L_2$ can be positioned alternatively about the phenyl, pyrimidinyl or pyridinyl moiety shown.

Without limitation, at least one of $E_1$-$E_3$ can be N. In certain embodiments, $E_1$ and $E_3$ can be N, and $E_5$ can be N. Regardless, Ar can be selected from fluoro-, chloro- and cyano-substituted phenyl moieties. In certain non-limiting embodiments, $L_1$ can be selected from $(CH_2)_n$ moieties, where n can be an integer selected from 1-3, and $CH(R_4)CH(R_5)CH(R_6)$ moieties where each of $R_4$-$R_6$ can be independently selected from H and fluoro substituents. In certain such embodiments, L$_2$ can be selected from (CH$_2$)$_m$ and CH(R$_7$)CH(R$_8$), moieties, where m can be an integer selected from 1-3 and each of R$_7$-R$_8$ can be independently selected from H and fluoro substituents.

In part, the present invention can also be directed to compounds of a formula

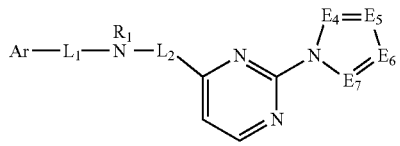

of salts thereof, wherein Ar, L$_1$, L$_2$ and E$_4$ -E$_7$ can independently be selected from moieties of the sort discussed above or illustrated elsewhere herein, and salts thereof.

In certain embodiments, without limitation, Ar can be selected from fluoro-, chloro- and cyano-substituted phenyl moieties, pyridinyl, methyl- and methyl- and amino-substituted pyridinyl moieties; L$_1$ can be selected from optionally substituted divalent C$_1$-C$_4$ alkylene moieties, where such substituents can be selected from halo, alkyl and divalent methylene substituents; L$_2$ can be selected from optionally fluoro-substituted divalent C$_1$-C$_3$ alkylene moieties; and E$_4$-E$_7$ can be independently selected from CH, CR$_3$ and N, providing at least one of E$_4$-E$_7$ is N, and where R$_3$ can be selected from methyl and halo substituents. In certain such embodiments, L$_1$ can be selected from (CH$_2$)$_n$ moieties, where n can be an integer selected from 1-3, CH(R$_4$)CH(R$_5$)CH(R$_6$) moieties where each of R$_4$-R$_6$ can be independently selected from H and fluoro substituents, and moieties where R$_4$ and R$_5$ can together and R$_5$ and R$_6$ can together form methylene substituents and cyclopropyl moieties. Regardless, L$_2$ can be selected from (CH$_2$)$_m$ and CH(R$_7$)CH(R$_8$) moieties, where m can be an integer selected from 1-3 and each of R$_7$-R$_8$ can be independently selected from H and fluoro substituents. Without limitation, E$_5$ can be N.

In part, the present invention can also be directed to compounds of a formula

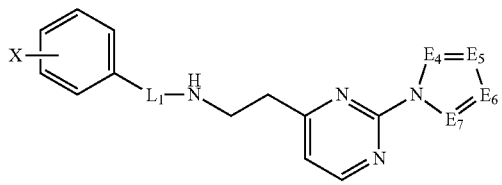

or salts thereof, wherein L$_1$ and E$_4$ -E$_7$ can be as discussed above or illustrated elsewhere herein; and X can be selected, without limitation, from fluoro, chloro, and cyano substituents. Regardless, L$_1$ can be selected from optionally-substituted divalent C$_1$-C$_4$ alkylene moieties, where said substituents can be selected from halo, alkyl and divalent methylene substituents; and E$_4$-E$_7$ can be independently selected from CH, CR$_3$ and N, providing at least one of E$_4$-E$_7$ is N, and where R$_3$ can be selected from methyl and halo substituents. In certain embodiments, E$_5$ can be N. In certain such embodiments, E$_4$ and E$_6$ can be independently selected from CH and CR$_3$ moieties, where each R$_3$ can be independently selected from methyl and chloro substituents.

Regardless, various compounds of this invention are without stereochemical limitation. As illustrated and discussed below, certain such compounds and/or their intermediates are available as racemic mixtures from which isomers can be resolved, or are diastereomers from which the corresponding enantiomers can be separated. Accordingly, any stereocenter can be (S) or (R) with respect to any other stereocenter(s). As a separate consideration, various compounds can be present as an acid salt, either partially or fully protonated. In certain such embodiments, the counterion(s) can be a conjugate base of a protic acid. Further, it will be understood by those skilled in the art that any one or more the compounds of this invention can be provided as part of a pharmaceutical composition comprising a pharmaceutically-acceptable carrier component for use in conjunction with a treatment method or medicament.

In part, the present invention can also be directed to a method inhibiting, modulating or otherwise affecting a nitric oxide synthase. Such a method can comprise providing a compound of this invention, whether or not part of a pharmaceutical composition, and administering an effective amount of such a compound and contacting a nitric oxide synthase therewith, such compounds including but not limited to those illustrated by the following examples, referenced figures and/or accompanying synthetic schemes. In certain embodiments, such contact can induce, promote or otherwise provide coordination of such a compound with hemoglobin iron in an active site of such a synthase. In certain such embodiments, such a compound and/or combination thereof can be present in an amount at least partially sufficient to selectively inhibit neuronal nitric oxide synthase over inducible and endothelial isoforms.

DETAILED DESCRIPTION OF THE DRAWINGS

FIG. 1. Compound (±)-1 (prior art) is a highly potent and selective nNOS inhibitor; however, it possess multiple charges. In accordance with certain non-limiting embodiments of this invention, compounds 2 and 3 provide new nNOS inhibitor scaffolds. (ND=not determined.)

Figure 2:
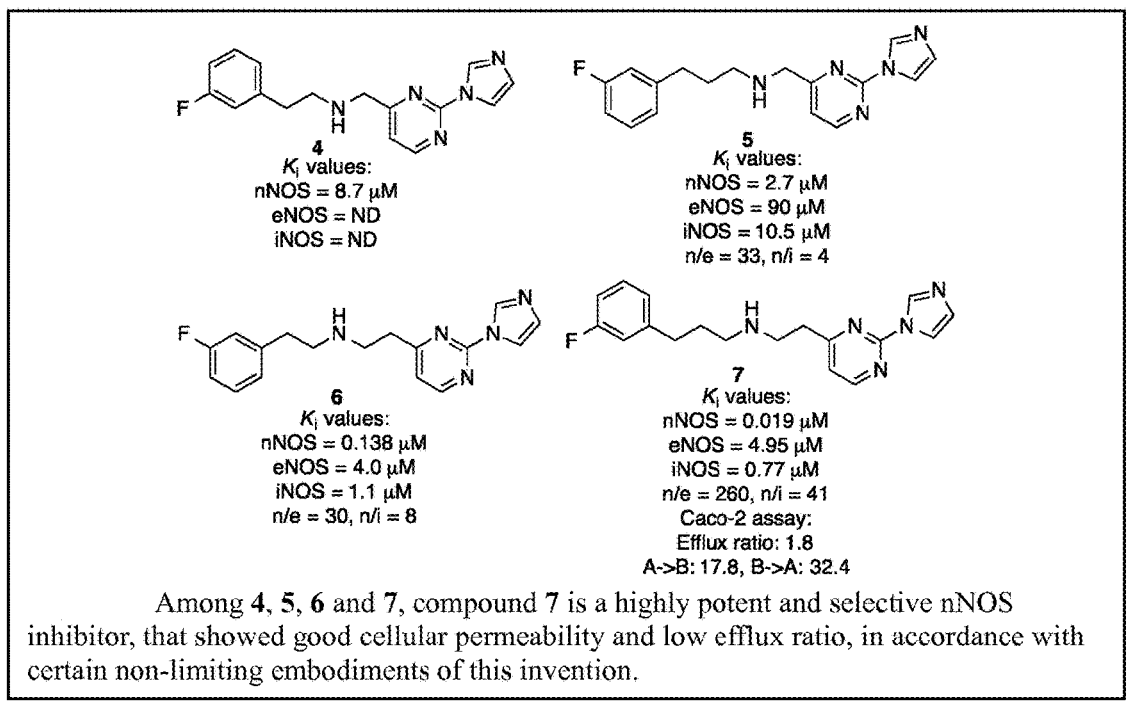

FIG. 2. Among 4, 5, 6 and 7, compound 7 is a highly potent and selective nNOS inhibitor, that showed good cellular permeability and low efflux ratio, in accordance with certain non-limiting embodiments of this invention.

Figure 3:
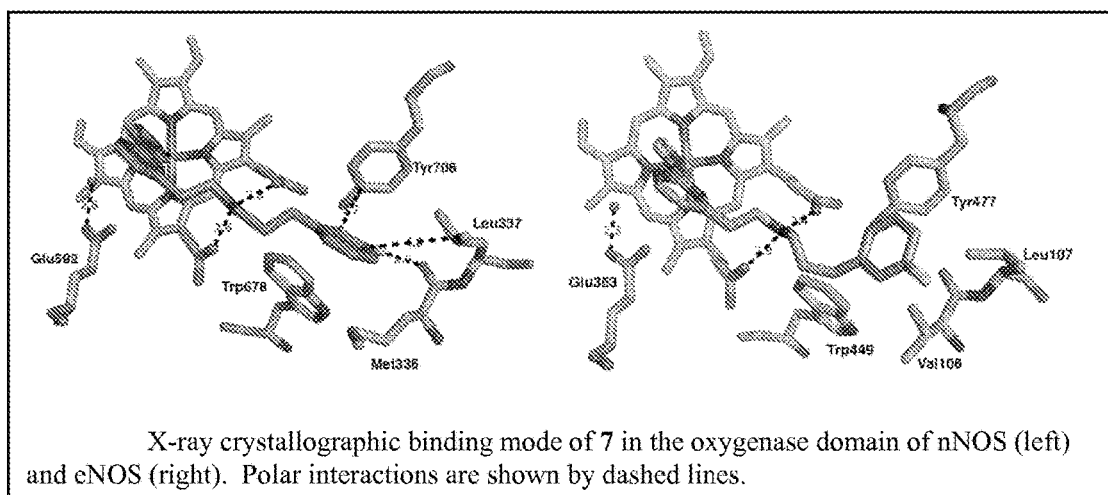

FIG. 3. Schematic illustration of X-ray crystallographic binding mode of compound 7 in the oxygenase domain of nNOS (left) and eNOS (right). Polar interactions are shown by dashed lines.

Figure 4:
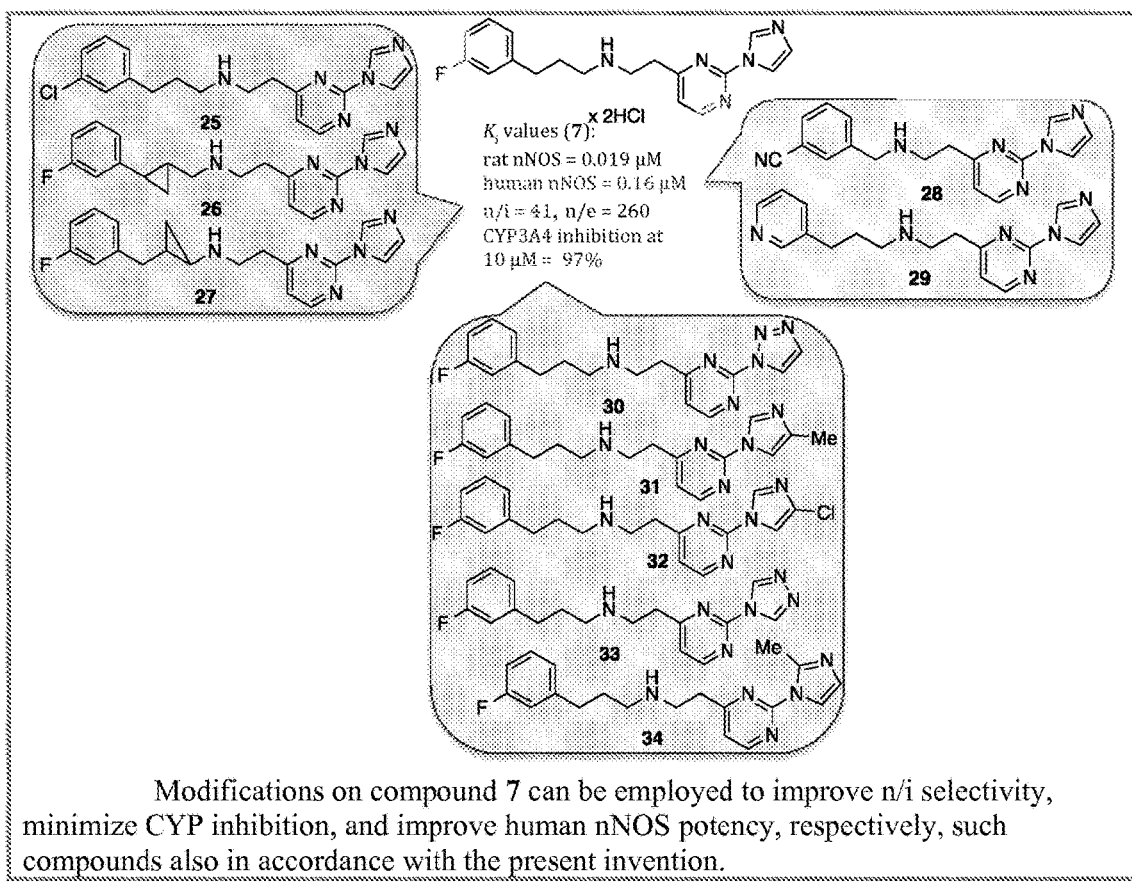

FIG. 4. Modifications on compound 7 can be employed to improve n/i selectivity, minimize cytochrome P (CYP) inhibition, and improve human nNOS potency, respectively, such compounds also in accordance with the present invention.

Figure 5:
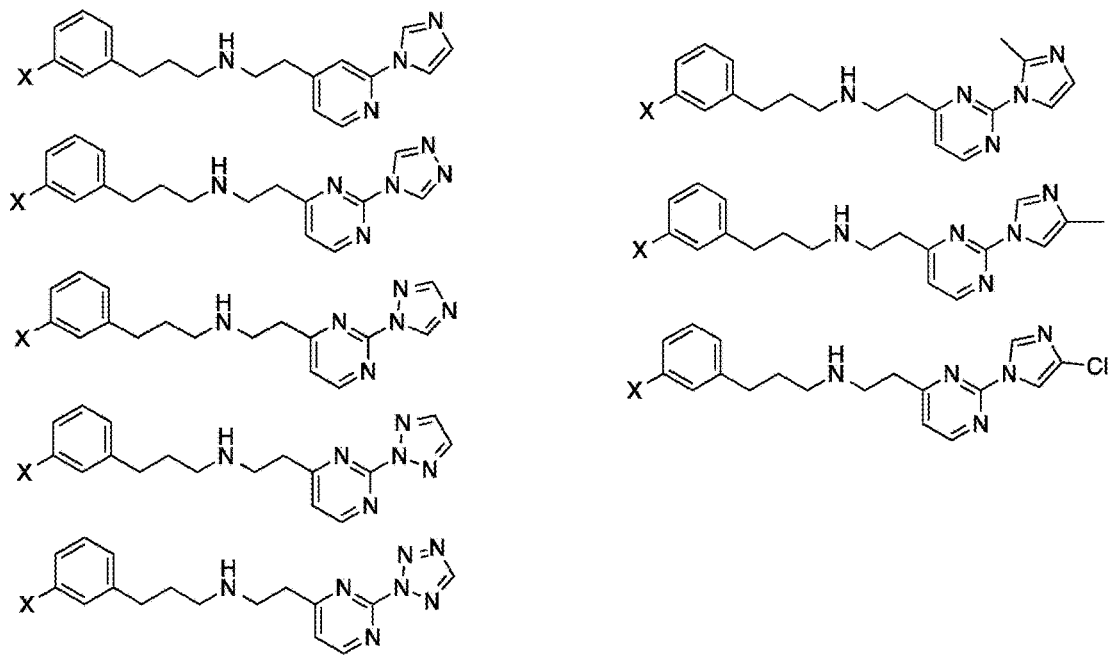
Figure 6:
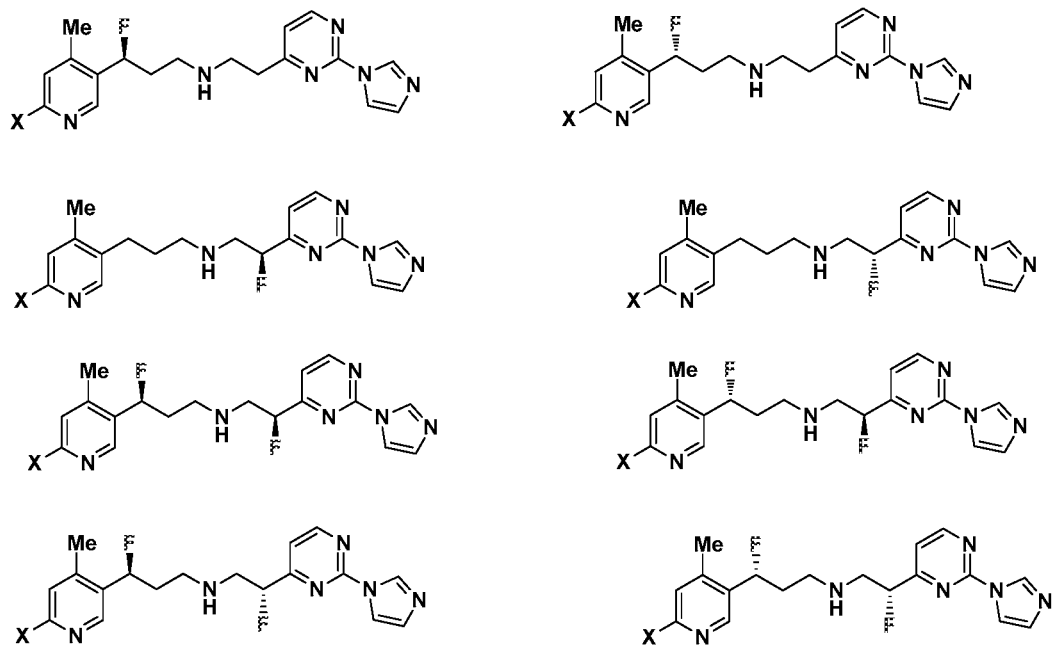

FIGS. 5 and 6. Various other compounds of this invention, in accordance with one or more non-limiting embodiments thereof.

DETAILED DESCRIPTION OF CERTAIN EMBODIMENTS

As previously mentioned, many of the highly potent and selective inhibitors of nNOS developed so far are arginine mimetics. As an example, compound 1 showed low nanomolar potency against rat nNOS and >800-fold selectivity over eNOS (FIG. 1). However, increased polar surface area, multiple charges, and >7-8 rotatable bonds adversely affect blood-brain barrier permeability. These drawbacks limit their further development as therapeutic candidates. Many modifications made on these pyrrolidinomethyl-2-aminopyridine scaffolds such as reducing the number of polar charges and basicity by alkylation, fluorination, intramolecular hydrogen-bonding, and simplification of the scaffold towards double-headed aminopyridine ligands were still unable to completely resolve permeability issues related to such compounds.

Therefore, in an attempt to find new scaffolds for nNOS inhibition, another class of pharmacophores was explored that exploit heme Fe-coordination in the active site with imidazole-containing ligands. Structure-activity studies with small molecules having such Fe-coordinating groups have not been done. Furthermore, there are no crystal structures of such compounds in nNOS to shed light on the binding modes of these ligands. Thus, the strategy employed to make new scaffolds was to replace the more polar pyrrolidinomethyl-2-aminopyridine head of 1 with a planar 2-imidazolylpyrimidine moiety, such as in compounds 2 and 3. Although compound 2 showed poor binding affinity to nNOS ($K_i$=4.7 µM), compound 3 showed a moderate submicromolar $K_i$ for nNOS with >100-fold selectivity over eNOS, but only 17-fold selectivity for iNOS.

Further modifications on 3 with respect to different linker lengths between 2-imidazolylpyrimidine and 3-fluorophenyl were conducted, together with reducing the number of basic amines (compounds 4 -7), to provide a highly potent inhibitor of nNOS (7, FIG. 2). X-ray crystallographic analysis of 7 in the rat nNOS active site revealed the following: a six-atom linker length was optimal between the 2-imidazolylpyrimidine and the hydrophobic aromatic end, the secondary amine at the homobenzylic position of the pyrimidine ring was equidistant between the two heme propionates to form a bifurcated hydrogen-bond with both (FIG. 3). The imidazole ring is perpendicular over the porphyrin plane with 2.1 Å distance from the central Fe. The propyl linker between the secondary amine group and the aromatic ring enables the 3-fluorophenyl ring to fit in the hydrophobic pocket lined by residues Met336, Leu337, and Tyr706 with electrostatic interactions between the ring and pocket residues. Contrary thereto, analysis of the crystal structure of 7 bound to eNOS showed that although the orientation of it up to the secondary amine is similar as in nNOS, beyond that the linker is disoriented, and the phenyl ring is pushed out of the pocket. This unstable orientation may account for the poor potency of 7 for eNOS.

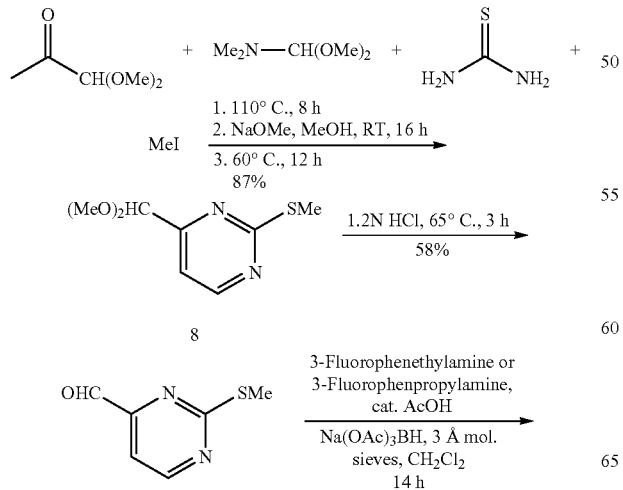

Scheme 1. Synthesis of compounds 4-5.

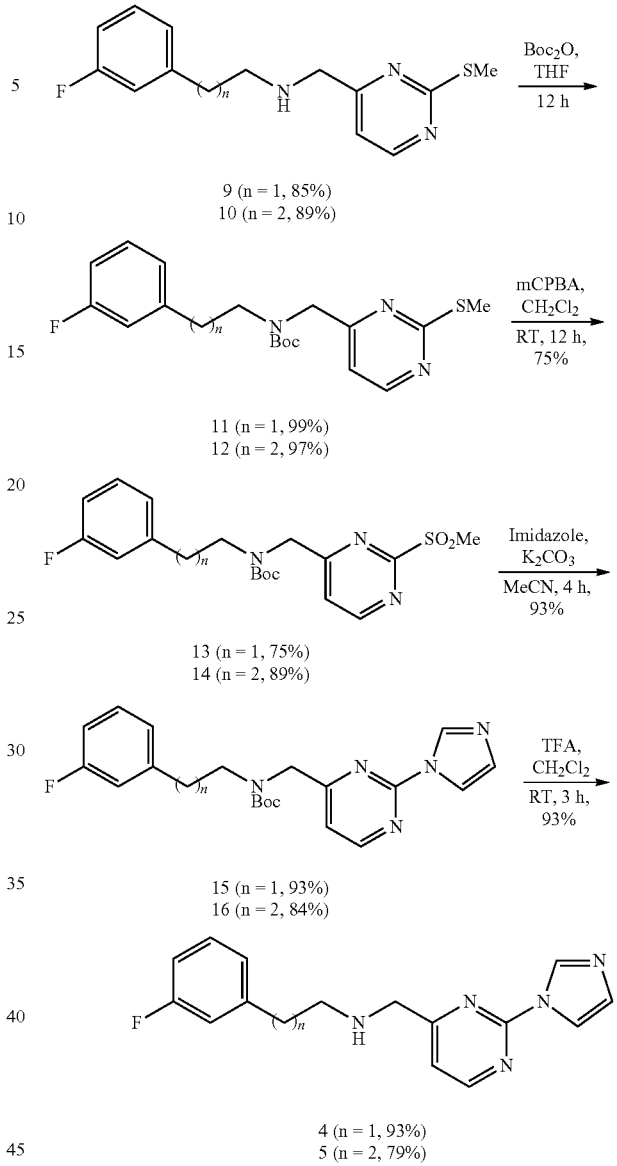

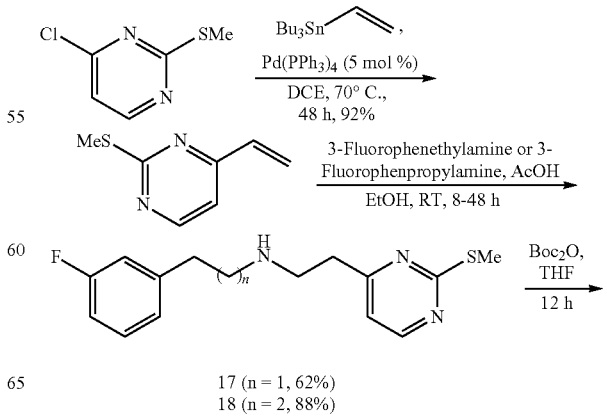

Scheme 2. Synthesis of compounds 6-7.

-continued

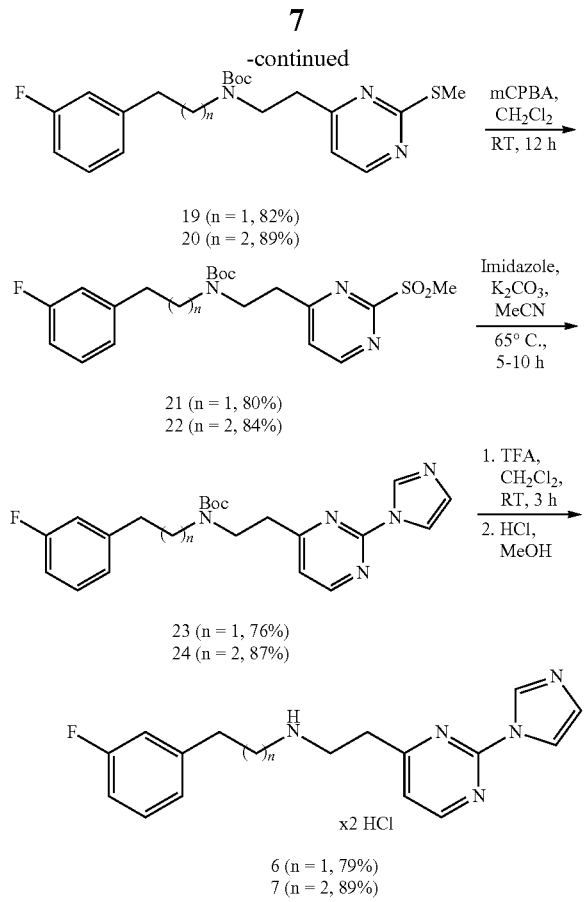

In comparison to the synthesis of previous nNOS inhibitors such as 1—requiring >15 steps, chiral resolutions, and separation of diastereomers—these 2-imidazolylpyrimdine scaffolds were synthesized in 6-7 steps with moderate to high yields. As a result, more structure-activity studies can be done in a shorter period of time. Scheme 1 depicts the synthetic route used to obtain 4-5, and Scheme 2 depicts the synthetic route to 6-7. Following reported literature procedures, compound 8 was synthesized, then acetal deprotection and reductive amination with the desired amines gave 9 and 10. Substitution by the imidazole ring, after protecting the secondary amine, gave the primary skeletal framework of 4 and 5. Similarly, starting from commercially available 4-chloro-2-methylthiopyrimidine, Stille coupling was employed to obtain the 2-methylthio-4-vinylpyrimidine, Michael addition on which provided 17-18 with the main skeletal structures of 6-7. Incorporation of the imidazole ring and deprotection gave the free bases 6 and 7. In addition to the low nanomolar potency of 7, and high selectivity against eNOS, it was very rewarding to see that it has membrane permeability and low efflux ratio in the caco-2 assay, which is related to brain membrane permeation. In addition, primary binding assays performed at 10 μM concentration on a panel of other CNS targets showed minimal inhibition for most of them, including the muscarinic receptors. (These assays were performed at the NIMH—Psychoactive Drug Screening Program (PDSP) at UNC-Chapel Hill. Secondary binding assays are in progress for the targets that showed >50% inhibition to determine an IC$_{50}$ value, which will provide more insight into the type of receptors it strongly binds to. This will shed light on the modification of the scaffold to avoid such off-target efficacy.)

Despite the high potency of 7 in rat nNOS and the improved permeability seen in Caco-2 assay compared to the previously reported nNOS inhibitors, the selectivity of 7 over iNOS was about 41-fold. Even so, an improved selectivity was desired. Considering the hydrophobic pocket near the substrate access channel in rat nNOS, which is rather hydrophilic and smaller in murine iNOS, due to the replacement of Leu337 with Asn115, this difference in residue can be utilized to impart some selectivity difference. Replacing the 3-fluoro substitution in 7 by a 3-chloro group as in 25 might provide the improved steric bulk to disfavor in iNOS (FIG. 4). This halogen exchange also provides an improved CLogP value for 25 over 7 with the same calculated polar surface area.

Furthermore, from the crystal structure obtained of 7 in the oxygenase domain of nNOS, and overlaying it with a crystal structure of iNOS (PDB code=1VAF), it is realized that the iNOS residues lining the targeted pocket region in nNOS imparts a smaller space for the inhibitor binding. Therefore, restricting 7 in its favored conformation by introducing a cyclopropyl ring at either the 1-2 or 2-3 positions of the propylamine chain (compounds 26-27) may disfavor binding to iNOS more and raise the n/i selectivity (FIG. 4).

In addition to the strong potency in rat nNOS, compound 7 also demonstrated a decent potency when assayed in human nNOS (K$_i$=0.193 μM), with nearly 8-fold selectivity for the rat over human isoform of nNOS. This difference in selectivity is assumed to arise from the difference in stabilization between the hydrophobic 3-fluorophenpropyl tail of 7 and the residues lining the hydrophobic pocket in rat nNOS (Met336, Leu337 and Tyr706), and the absence of such interactions between 7 and human nNOS. This is because in human nNOS, this equivalent region is smaller and more hydrophilic due to the presence of His342 residue in place of Leu337. Such results suggest further modifications on 7 to improve its potency for human nNOS while maintaining the potency also in the rat isoform. Compounds 28-29 contain 3-cyano or a 3-pyridyl group instead of the 3-fluorophenyl in 7, such that it can engage in an hydrogen-bonding interaction with the imidazole ring of His342 in human nNOS, while its aromatic end can still maintain some binding stabilizations in the hydrophobic pocket in rat nNOS—to lessen the selectivity between the human and rat isoforms of nNOS.

Compound 7 was promiscuous to some of the liver microsomal cytochrome P450 (P450) enzymes at 10 μM concentration. This promiscuity is speculated to arise from the 2-imidazolyl fragment in 7, since imidazole is a known heme-Fe coordinating ligand and therefore at 10 μM concentration, it can bind in the active site of the P450 enzymes. Therefore, determining an IC$_{50}$ value to judge its potency towards the cytochrome P (CYP) enzymes, and modification of the 2-imidazolyl fragment of 7 to alleviate its binding to CYPs was considered.

To understand the role of the imidazole ring in imparting its potency in 7, and its effect on the CYP enzymes, compounds 30-34 were designed, where the imidazole is replaced by a less donating 1,2,3- or 1,3,4-triazole ring, or a more donating 4-methyl or 2-methylimidazolyl group. The trend in difference in potency between 7, and 30-34 can be evaluated both in nNOS and in CYP3A4.

Scheme 3. General route to synthesize compounds 25-34. In case of 30-34, imidazole was replaced by the corresponding triazole or substituted-imidazole nucleophiles.

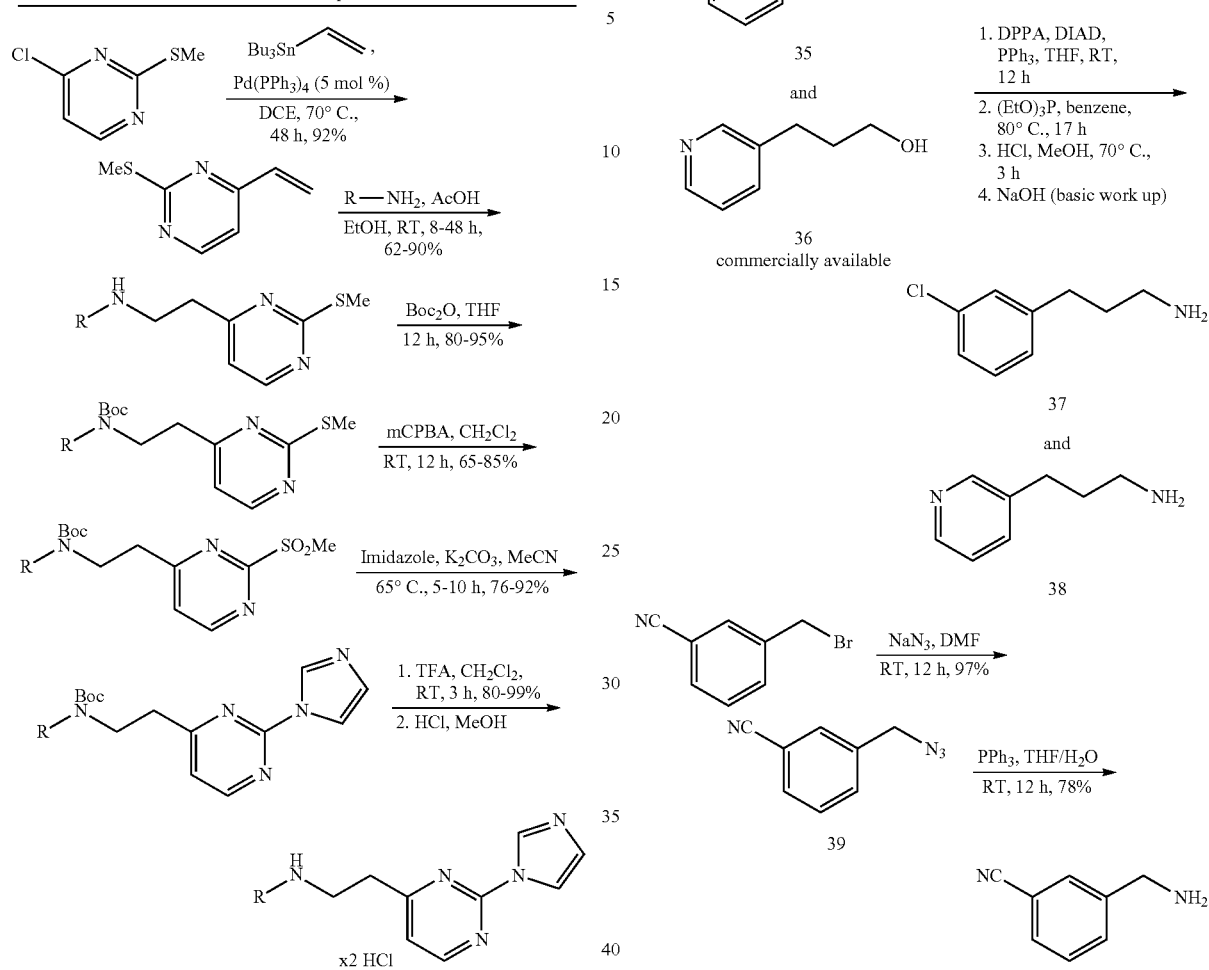

Syntheses of compounds 25-34 were initiated following the same general route as used to synthesize 7 (Scheme 3, above). Synthesis of the primary amines required to couple with the 2-methylthio-4-vinyl pyrimidine were synthesized from commercially available bromides, alcohols or carboxylic acids following methods shown in Scheme 4, below. To obtain the pure trans-isomers of the pure amines 42 and 44, the cis and trans diastereomers from the metal-catalyzed cyclopropanation step were separated by column chromatography, and identified with the help of 1D and 2D-NMR experiments (gCOSY, DEPT, HSQC, and 1D-NOESY). These pure isomers were then carried forward to form the amines.

Scheme 4. Synthesis of the primary amines 37-38, 40, 42, and 44.

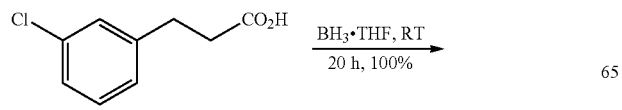

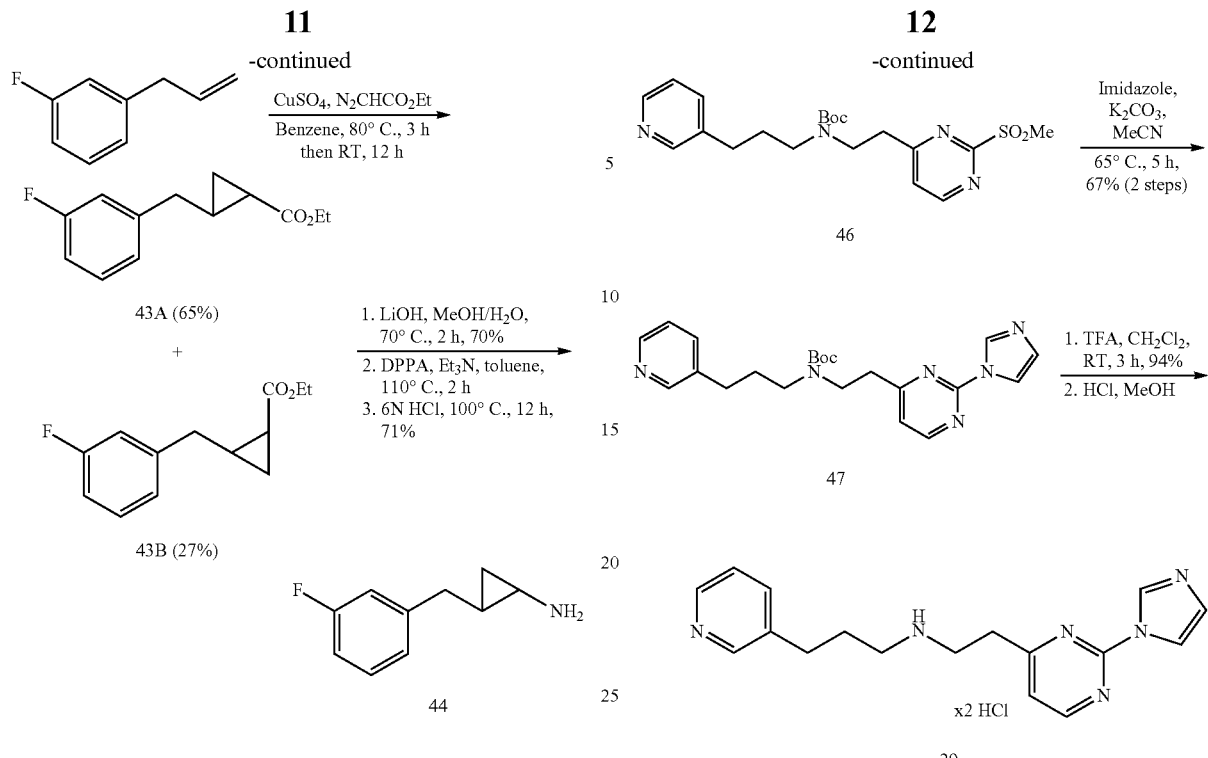

Syntheses of the final compounds (25-28, 30-33) have been achieved as their dihydrochloride salts following steps shown in Scheme 3. Synthesis of compound 29 followed a slightly modified route as outlined in Scheme 5. mCPBA oxidation of the intermediate 45 gave pyridine N-oxide along with oxidation of the thioether to sulfone. Changing the oxidant to oxone and optimizing the reaction condition gave selective oxidation of the thioether that was carried to the next step without further purification. Displacement of the sulfone by imidazole, followed by TFA deprotection of the Boc group and treatment with methanolic HCl gave the final dihydrochloride salt, 29.

Scheme 5. Synthesis of 29.

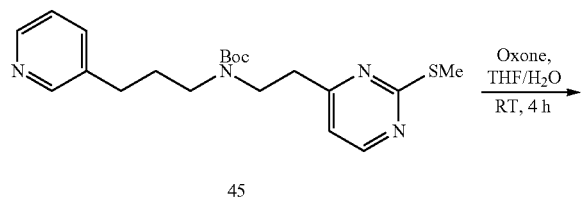

Hemoglobin capture assay performed to determine $IC_{50}$ values of the inhibitors, thereafter using the Cheng-Prusoff equation to determine the $K_i$ was performed on compounds 25-31 (Table 1). Replacing the 3-F with a 3-Cl did not alter much in the potency or selectivity, however with the cyclopropyl ring a- to the secondary amine showed an improved selectivity over eNOS and iNOS, without much change in potency.

With more hydrophilic aromatic ends, indeed compounds 28 and 29 showed a lower human nNOS/rat nNOS selectivity ratio, where compound 29 does exhibit good potency for both the human and rat nNOS isoforms.

Furthermore, when the imidazole ring is replaced with a 4-methylimidazole as in 31, although potency for nNOS is compromised to 667 nM, CYP3A4 inhibition is also reduced considerably (for 7; CYP3A4 $IC_{50}$=3 µM; for 31; CYP3A4 $IC_{50}$=15 µM). These results are encouraging for further investigation.

TABLE 1

NOS enzyme assay results (NT = Not Tested; ND = Not Determined).

| Compound | $K_i$ (µM) | | | | Ratios | |
| --- | --- | --- | --- | --- | --- | --- |
| | nNOS | eNOS | iNOS | hnNOS | n/e | n/i |
| 2 | 4.7 | NT | NT | NT | NA | NA |

TABLE 1-continued
NOS enzyme assay results (NT = Not Tested; ND = Not Determined).
| Compound | K$_i$ (μM) | | | | Ratios | |
| --- | --- | --- | --- | --- | --- | --- |
| | nNOS | eNOS | iNOS | hnNOS | n/e | n/i |
| 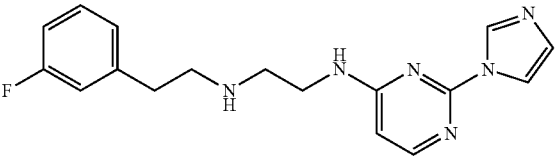 [SMILES: Fc1cccc(CCNCCNc2ccnc(-n3ccnc3)n2)c1] 3 | 0.37 | 40 | 6.4 | NT | 109 | 17 |
| 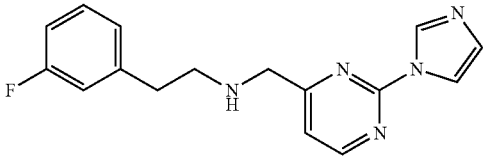 [SMILES: Fc1cccc(CCNCc2ccnc(-n3ccnc3)n2)c1] 4 | 8.7 | NT | NT | NT | NA | NA |
| 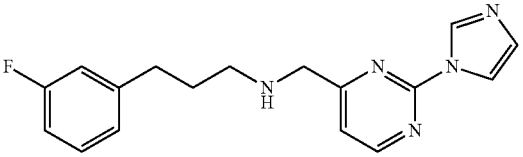 [SMILES: Fc1cccc(CCCNCc2ccnc(-n3ccnc3)n2)c1] 5 | 2.7 | 90 | 10.5 | NT | 33 | 4 |
| 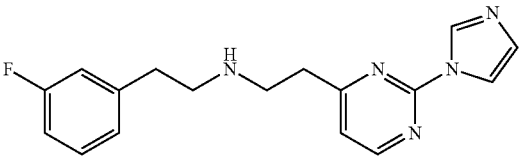 [SMILES: Fc1cccc(CCNCCc2ccnc(-n3ccnc3)n2)c1] 6 | 0.138 | 4 | 1.1 | 0.758 | 30 | 8 |
| 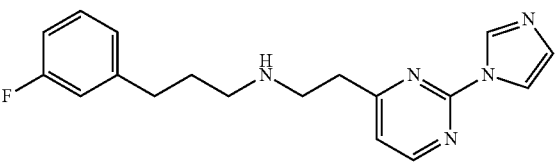 [SMILES: Fc1cccc(CCCNCCc2ccnc(-n3ccnc3)n2)c1] 7 | 0.019 | 4.95 | 0.77 | 0.193 | 260 | 41 |
| 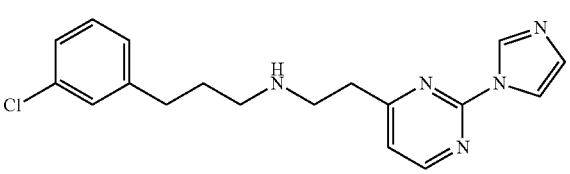 [SMILES: Clc1cccc(CCCNCCc2ccnc(-n3ccnc3)n2)c1] 25 | 0.032 | 8.1 | 2.0 | 0.125 | 253 | 28 |
| 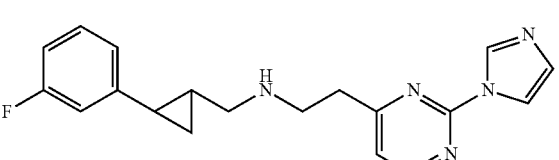 26 | 0.056 | 4.0 | 1.9 | 0.359 | 71 | 34 |

TABLE 1-continued

NOS enzyme assay results (NT = Not Tested; ND = Not Determined).

| Compound | $K_i$ (μM) | | | | Ratios | |
| --- | --- | --- | --- | --- | --- | --- |
| | nNOS | eNOS | iNOS | hnNOS | n/e | n/i |
| 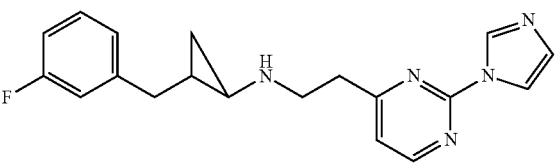 [SMILES: Fc1cccc(CC2CC2NCCc2ccnc(-n3ccnc3)n2)c1] 27 | 0.040 | 14.5 | 2.9 | 0.358 | 363 | 73 |
| 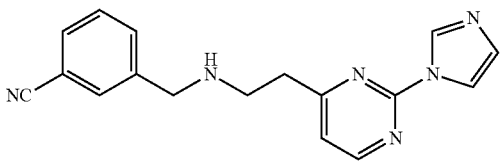 [SMILES: N#Cc1cccc(CNCCc2ccnc(-n3ccnc3)n2)c1] 28 | 0.183 | 10.5 | 3.4 | 0.138 | 57 | 19 |
| 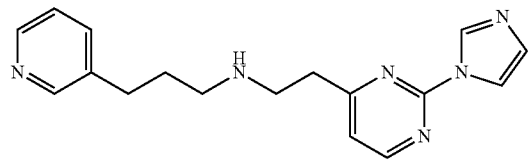 [SMILES: c1cncc(CCCNCCc2ccnc(-n3ccnc3)n2)c1] 29 | 0.054 | 10.9 | 1.8 | 0.125 | 202 | 33 |
| 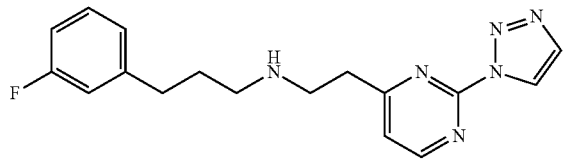 [SMILES: Fc1cccc(CCCNCCc2ccnc(-n3ccnn3)n2)c1] 30 | 60 | NT | NT | NT | ND | ND |
| 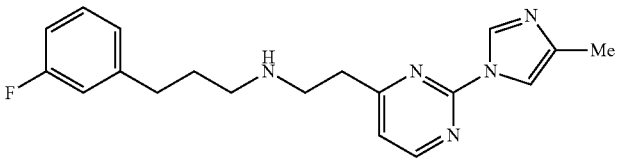 [SMILES: Cc1cn(-c2nccc(CCNCCCc3cccc(F)c3)n2)cn1] 31 | 0.667 | 171 | 287 | 4.49 | 256 | 430 |
| 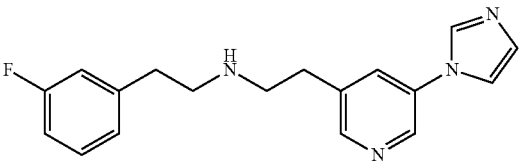 [SMILES: Fc1cccc(CCNCCc2cncc(-n3ccnc3)c2)c1] 48 | 5.5 | NT | NT | NT | ND | ND |

Various amine starting materials can be prepared via the synthetic techniques outlined in Scheme 4 or straightforward variations thereof. With reference to Schemes 1-3, reductive amination of a pyrimidinyl aldehyde or Michael addition to a vinyl pyrimidine with such an amine can provide a substituted pyrimidine core. Azole incorporation affords, for example, a target imidazolyl-pyrimidine scaffold. In accordance with certain non-limiting embodiments of this invention, various other non-limiting representative compounds, as can be used for selective nNOS inhibition, are shown in FIGS. 5 and 6. (X=e.g., halogen, CN, amino and methyl).

Methods of the present invention can also, as would be understood by those skilled in the art, be extended to or include methods using or in conjunction with a pharmaceutical composition comprising an inhibitor compound of the sort described herein and a physiologically or otherwise suitable formulation. In a some embodiments, the present invention includes one or more NOS inhibitors, as set forth above, formulated into compositions together with one or more physiologically tolerable or acceptable diluents, carriers, adjuvants or vehicles that are collectively referred to herein as carriers. Compositions suitable for such contact or administration can comprise physiologically acceptable sterile aqueous or nonaqueous solutions, dispersions, suspensions or emulsions. The resulting compositions can be, in conjunction with the various methods described herein, for administration or contact with a cellular medium, bacterium and/or a nitric oxide synthase expressed or otherwise present therein. Whether or not in conjunction with a pharmaceutical composition, "contacting" means that a nitric oxide synthase and one or more inhibitor compounds are brought together for purpose of binding and/or complexing such an inhibitor compound to the enzyme. Amounts of a compound effective to inhibit a nitric oxide synthase may be determined empirically, and making such determinations is within the skill in the art. Modulation, inhibition or otherwise affecting nitric oxide synthase activity includes both reduction and/or mitigation, as well as elimination of NOS activity and/or nitric oxide production.

It is understood by those skilled in the art that dosage amount will vary with the activity of a particular inhibitor compound, disease state, route of administration, duration of treatment, and like factors well-known in the medical and pharmaceutical arts. In general, a suitable dose will be an amount which is the lowest dose effective to produce a therapeutic or prophylactic effect. If desired, an effective dose of such a compound, pharmaceutically-acceptable salt thereof, or related composition may be administered in two or more sub-doses, administered separately over an appropriate period of time.

Methods of preparing pharmaceutical formulations or compositions include the step of bringing an inhibitor compound into association with a carrier and, optionally, one or more additional adjuvants or ingredients. For example, standard pharmaceutical formulation techniques can be employed, such as those described in Remington's Pharmaceutical Sciences, Mack Publishing Company, Easton, Pa.

Regardless of composition or formulation, those skilled in the art will recognize various avenues for medicament administration, together with corresponding factors and parameters to be considered in rendering such a medicament suitable for administration. Accordingly, with respect to one or more non-limiting embodiments, the present invention provides for use of one or more nitric oxide synthase inhibitor compounds for the manufacture of a medicament for therapeutic use in the treatment of various disease states, in particular neurodegenerative diseases.

While the principles of this invention have been described in connection with specific embodiments, it should be understood clearly that these descriptions are provided only by way of example and are not intended to limit, in any way, the scope of this invention. For instance, while the utility of this invention is illustrated through the use of several compounds, moieties thereof and/or substituents thereon, it will be understood by those skilled in the art that comparable results are obtainable with various other compounds, moieties and/or substituents, as are commensurate with the scope of this invention.

We claim:

1. A method of inhibiting a nitric oxide synthase, said method comprising:
(a) providing a compound of a formula

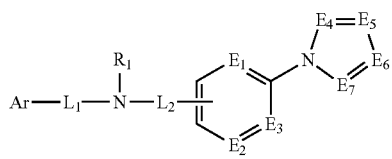

wherein Ar is selected from optionally-substituted aryl and heteroaryl moieties, where said substituents are selected from halo, alkyl, haloalkyl, cyano and amino substituents; $L_1$ is selected from optionally-substituted divalent $C_1$-$C_4$ alkylene moieties, where said substituents are selected from halo, alkyl and divalent methylene substituents; $R_1$ is selected from H, alkyl and divalent alkylene substituents and amino protecting groups; $L_2$ is selected from optionally-substituted divalent $C_1$-$C_3$ alkylene moieties, where said substituents are selected from halo, aza (—NH—) and substituted aza (—NR$_2$) moieties, where $R_2$ is selected from alkyl and divalent alkylene substituents; $E_1$ and $E_3$ are N, and $E_2$ is CH; and $E_4$-$E_7$ are independently selected from CH, CR$_3$ and N, providing at least one of $E_4$-$E_7$ is N, and where $R_3$ is selected from methyl and halo substituents, or a salt of a said compound; and
(b) contacting said compound with a nitric oxide synthase.

2. The method of claim 1 wherein Ar is selected from fluoro-, chloro- and cyano-substituted phenyl moieties; and $E_5$ is N.

3. The method of claim 2 wherein $E_6$ is a CCH$_3$ moiety.

4. A method of inhibiting a nitric oxide synthase, said method comprising:
(a) providing a compound of a formula

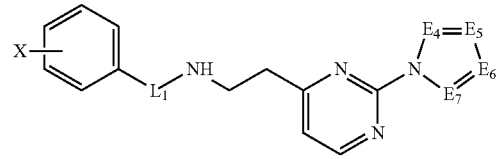

wherein X is selected from fluoro-, chloro- and cyano-substituents; $L_1$ is selected from optionally-substituted divalent $C_1$-$C_4$ alkylene moieties, where said substituents are selected from halo, alkyl and divalent methylene substituents; and $E_4$-$E_7$ are independently selected from CH, CR$_3$ and N, providing at least one of $E_4$-$E_7$ is N, and where $R_3$ is selected from methyl and halo substituents, or a salt of a said compound; and
(b) contacting said compound with a nitric oxide synthase, thereby inducing coordination of said compound with hemoglobin iron in an active site of said nitric oxide synthase.

5. The method of claim 4 wherein $E_5$ is N.

6. The method of claim 5 wherein $E_6$ is a CCH$_3$ moiety.

7. The method of claim 4 wherein neuronal nitric oxide synthase is selectively inhibited over inducible and endothelial isoforms.

8. The method of claim 1 wherein $L_1$ is selected from $(CH_2)_n$ moieties, where n is an integer selected from 1-3, CH(R$_4$)CH(R$_5$)CH(R$_6$) moieties where each of R$_4$-R$_6$ is independently selected from H, fluoro, and alkyl substituents and moieties where R$_4$ and R$_5$ together and R$_5$ and R$_6$ together form methylene substituents and cyclopropyl moieties.

9. The method of claim 1 wherein $L_2$ is selected from $(CH_2)_m$, CH(R$_7$)CH(R$_8$), $(CH_2)_m$NH and $(CH_2)_m$NR$_2$ moieties, where m is an integer selected from 1-3 and each of R$_7$-R$_8$ is independently selected from H and fluoro substituents, and moieties where R$_1$ and R$_2$ together form a divalent $C_1$-$C_2$ alkylene substituent and a diazacycloalkyl moiety.

10. The method of claim 1 wherein $L_1$ is selected from $(CH_2)_n$ moieties, where n is an integer selected from 1-3, and CH($R_4$)CH($R_5$)CH($R_6$) moieties where each of $R_4$-$R_6$ is independently selected from H and fluoro substituents.

11. The method of claim 1 wherein $L_2$ is selected from $(CH_2)_m$ and CH($R_7$)CH($R_8$), moieties, where m is an integer selected from 1-3 and each of $R_7$-$R_8$ is independently selected from H and fluoro substituents.

12. The method of claim 1 wherein said compound is an ammonium salt, and said salt has a counter ion that is a conjugate base of a protic acid.

13. The method of claim 4 wherein $L_1$ is selected from $(CH_2)_n$ moieties, where n is an integer selected from 1-3, and CH($R_4$)CH($R_5$)CH($R_6$) moieties where each of $R_4$-$R_6$ is independently selected from H and fluoro substituents.

14. The method of claim 4 wherein said compound is an ammonium salt, and said salt has a counter ion that is a conjugate base of a protic acid.

15. A method of inhibiting a nitric oxide synthase, said method comprising:

(a) providing a compound of a formula

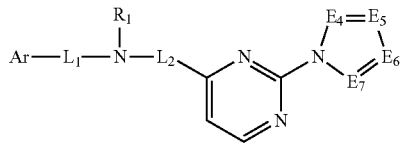

wherein Ar is selected from fluoro-, chloro- and cyano-substituted phenyl moieties, pyridinyl, methyl- and methyl- and amino-substituted pyridinyl moieties; $L_1$ is selected from optionally substituted divalent $C_1$-$C_4$ alkylene moieties, where said substituents are selected from halo, alkyl and divalent methylene substituents; $L_2$ is selected from optionally fluoro-substituted divalent $C_1$-$C_3$ alkylene moieties; and $E_4$-$E_7$ are independently selected from CH, $CR_3$ and N, providing at least one of $E_4$-$E_7$ is N, and where $R_3$ is selected from methyl and halo substituents, or a salt of a said compound; and (b) contacting said compound with a nitric oxide synthase.

16. The compound of claim 15 wherein $L_1$ is selected from $(CH_2)_n$ moieties, where n is an integer selected from 1-3, CH($R_4$)CH($R_5$)CH($R_6$) moieties where each of $R_4$-$R_6$ is independently selected from H and fluoro substituents, and moieties where $R_4$ and $R_5$ together and $R_5$ and $R_6$ together form methylene substituents and cyclopropyl moieties.

17. The compound of claim 15 wherein $L_2$ is selected from $(CH_2)_m$, CH($R_7$)CH($R_8$), $(CH_2)_m$NH and $(CH_2)_m$$NR_2$ moieties, where m is an integer selected from 1-3 and each of $R_7$-$R_8$ is independently selected from H and fluoro substituents, and moieties where $R_1$ and $R_2$ together form a divalent $C_1$-$C_2$ alkylene substituent and a diazacycloalkyl moiety.

18. The compound of claim 15 wherein $E_5$ is N.

19. The compound of claim 15 wherein $L_1$ is selected from $(CH_2)_n$ moieties, where n is an integer selected from 1-3, and CH($R_4$)CH($R_5$)CH($R_6$) moieties where each of $R_4$-$R_6$ is independently selected from H and fluoro substituents;.

20. The compound of claim 15 wherein $L_2$ is selected from $(CH_2)_m$ and CH($R_7$)CH($R_8$), moieties, where m is an integer selected from 1-3 and each of $R_7$-$R_8$ is independently selected from H and fluoro substituents.

* * * * *